United States Patent
Ford

Patent Number: 5,498,034
Date of Patent: Mar. 12, 1996

[54] PATIENT CARE INFORMATION SYSTEM

[76] Inventor: Betheline Ford, 19300 N. Portland, Edmond, Okla. 73003

[21] Appl. No.: 137,642

[22] Filed: Oct. 15, 1993

[51] Int. Cl.⁶ .................. G09F 3/00; A61B 5/00
[52] U.S. Cl. .................. 253/67; 283/70; 434/262
[58] Field of Search .................. 434/262, 428, 434/430, 112; 206/459.5; 40/152; 283/900, 67, 70

[56] References Cited

U.S. PATENT DOCUMENTS

| | | | |
|---|---|---|---|
| 302,104 | 7/1884 | Clinedinst | 40/159 |
| 324,164 | 8/1885 | Raisbeck | 40/159 |
| 3,651,512 | 3/1972 | Summers | 434/112 X |
| 4,165,890 | 8/1979 | Leff | 434/112 X |
| 4,761,633 | 8/1988 | Leff et al. | 434/112 X |
| 4,795,348 | 1/1989 | Garthwaite | 434/430 X |
| 4,865,549 | 9/1989 | Sonsteby | 434/262 |
| 4,954,083 | 9/1990 | Leff et al. | 434/112 |
| 4,994,968 | 7/1990 | Wagner | 40/159 X |
| 5,031,937 | 7/1991 | Nellhaus | 283/900 X |
| 5,096,752 | 3/1992 | Wagner | 40/152 X |
| 5,127,756 | 7/1992 | Lumm | 283/900 X |

FOREIGN PATENT DOCUMENTS

| | | | |
|---|---|---|---|
| 830480 | 3/1960 | United Kingdom | 434/428 |

*Primary Examiner*—Frances Han
*Attorney, Agent, or Firm*—Dunlap & Codding

[57] ABSTRACT

A patient care information system which includes a plurality of patient care block assemblies with each block assembly having a patient care symbol thereon indicating patient information relating to the providing of care for the patient. Predetermined ones of the patient care block assemblies are selected relating to the care of a selected patient and those patient care block assemblies so selected are designated as selected patient care block assemblies. The selected patient care block assemblies are displayed in the vicinity of the selected patient where the patient care symbols on the selected patient care block assemblies are available to a care provider rendering care to the selected patient.

27 Claims, 4 Drawing Sheets

FIG. 1

SENSORY LOSSES

NO TEETH

DENTURES

HARD OF HEARING

USES HEARING AID

CANNOT TALK

WEARS GLASSES

BLIND

PARALIZED / WEAKSIDE

MOBILITY ACTIVITY

ONE MAN TRANSFER

TWO MAN TRANSFER

UP IN WHEELCHAIR

UP IN CHAIR

AMBULATORY

USES WALKER

TURN EVERY TWO HOURS

SAFETY

WEDGE CUSHION IN CHAIR

SEAT BELT IN CHAIR

POSEY VEST IN CHAIR

NO BED RAILS

HEAD OF BED ELEVATED

CONFUSED

WANDERS

Fig. 2

ADL ACTIVITIES

TUB BATH
TUB

WHIRLPOOL BATH
WHPL

SHOWER BATH

INCONTINENT

BOWEL AND BLADDER TRAINING

RANGE OF MOTION Q SHIFT

PRECAUTIONS

WOUND DRESSING

MEDICATED PATCH

SPECIAL INSTRUCTIONS

SPECIAL HANDWASHING

PRESSURE MATTRESS

PHYSICAL THERAPY

MEALS

NOTHING BY MOUTH

SPOON FEED

ASSIST WITH MEALS

FORCE FLUIDS

RESTRICT FLUIDS

SALT RESTRICTED DIET

DIABETIC DIET

SPECIAL DIET

PATIENT CARE INFORMATION SYSTEM

FIELD OF THE INVENTION

The present invention relates generally to devices for assisting in the providing of care to patients and, more particularly, but not by way of limitation, to a system which includes a plurality of patient care block assemblies with each of the block assemblies having a patient care pictorial symbol thereon indicating patient information relating to the providing of care for a particular selected patient and wherein selected ones of the patient block assemblies are displayed in the vicinity of the selected patient to assist a care provider in rendering care to the selected patient.

BRIEF DESCRIPTION OF THE DRAWINGS

FIG. 2A is a continuation of FIG. 2.

DESCRIPTION OF THE PREFERRED EMBODIMENTS

Figure 1:
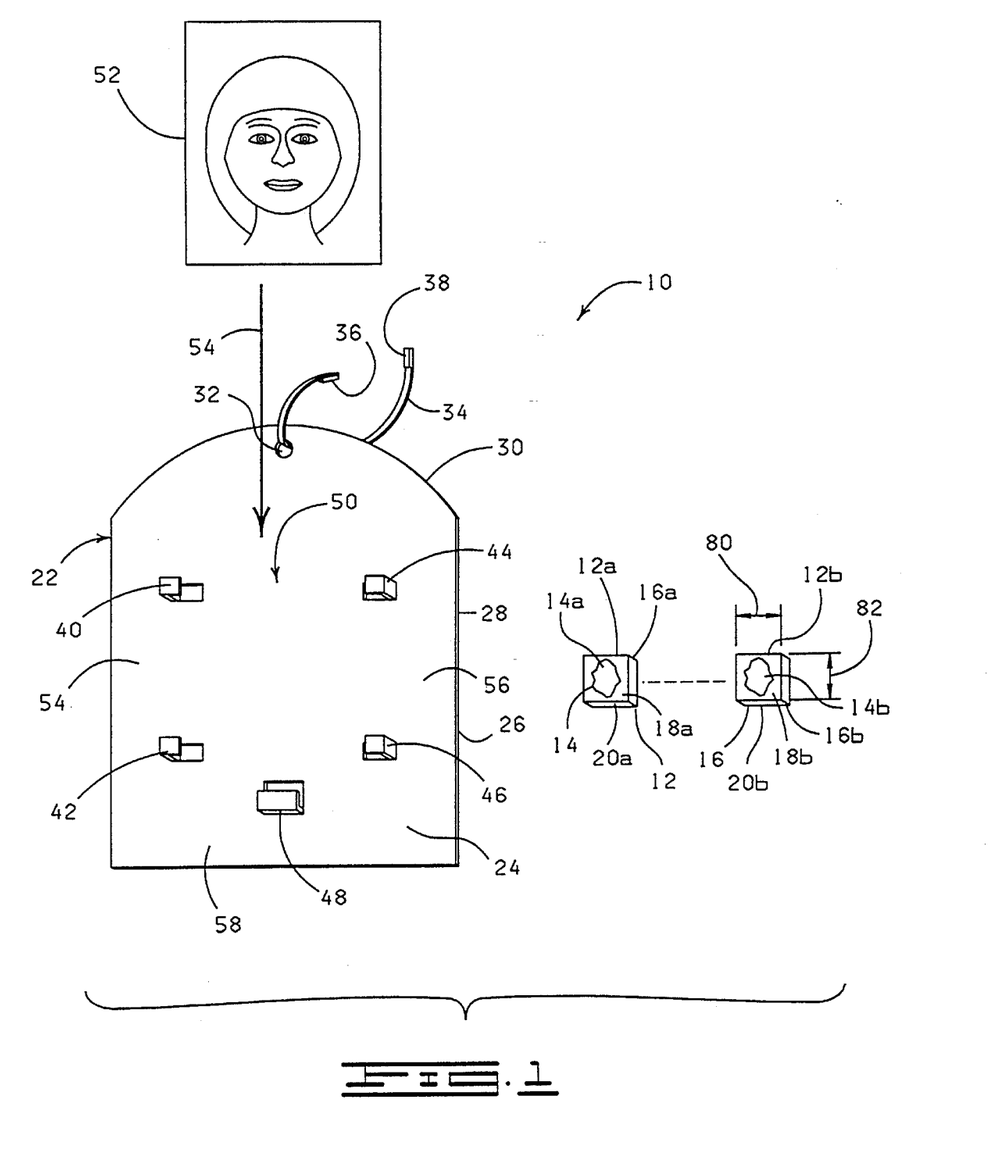
FIG. 1 is a view of a patient care information assembly constructed in accordance with the present invention.

Shown in FIG. 1 and designated by the general reference numeral 10 is a patient care information assembly constructed in accordance with the present invention. The patient care information assembly 10 includes a plurality of patient care block assemblies 12. Only two patient care block assemblies 12 are shown in FIG. 1 and designated with the individual reference numerals 12a and 12b. Each of the patient care block assemblies 12 has a patient care pictorial symbol 14 on a portion thereof. The particular patient care pictorial symbols 14 on the patient care block assemblies 12a and 12b are designated in FIG. 1 by the respective reference numerals 14a and 14b.

The term "patient" as used herein alone or in combination with other words includes patients, clients, residents and consumers, and, in general means a person receiving care.

Each of the patient care block assemblies 12 includes a patient care block 16 with the individual patient care blocks shown in FIG. 1 being designated by the individual reference numerals 16a and 16b. Each patient care block 16 has an upper surface 18 and a lower surface 20 (the individual upper and lower surfaces being designated in FIG. 1 by the respective reference numerals 18a, 18b, 20a and 20b with respect to the individual patient care blocks 16a and 16b). The patient care pictorial symbol 14a is printed on the upper surface 18a of the patient care block 14a. The patient care pictorial symbol 14b is printed on the upper surface 18b of the patient care block 16b.

Each of the patient care blocks 16 is constructed of a magnetic material for magnetically attaching the patient care block 16 to a metal surface.

The patient care information assembly 10 also includes a patient frame 22. The patient frame 22 is basically square or rectangularly shaped and has an upper surface 24 and a lower surface 26. The patient frame 22 has an outer peripheral edge 28 defining the square or rectangular shape of the patient frame 22. The patient frame 22 is constructed of a metal suitable for magnetically connecting one of the patient care blocks 16 to the upper surface 24 of the patient frame 22.

An arcuately shaped tab 30 is an integral extension of an upper end of the patient frame 22. The tab 30 extends a distance from the upper end of the patient frame 22. A hole 32 is formed through the tab 30 portion of the patient frame 22.

A strap 34 is extended through the opening 32. Hook and loop type fastening elements 36 and 38 are secured to the opposite ends of the strap 34 for removably connecting the opposite ends of the strap 34.

Five tabs 40, 42, 44, 46, and 48 are formed in the patient frame 22. Each of the tabs 40, 42, 44, 46, and 48 extends a distance upwardly from the upper surface 24 of the patient frame 22. Each of the tabs 40, 42, 44, 46, and 48 includes a portion at the outer most end thereof which extends a distance at an angle about parallel to the upper surface 24 of the patient frame 22. The tabs 40, 42, 44, 46, and 48 are sized and arranged on the upper surface 24 of the patient frame 22 to form a picture receiving channel 50 which is sized to receive a picture 52 of a selected patient. The picture 52 may be a photograph, for example.

Figure 2:
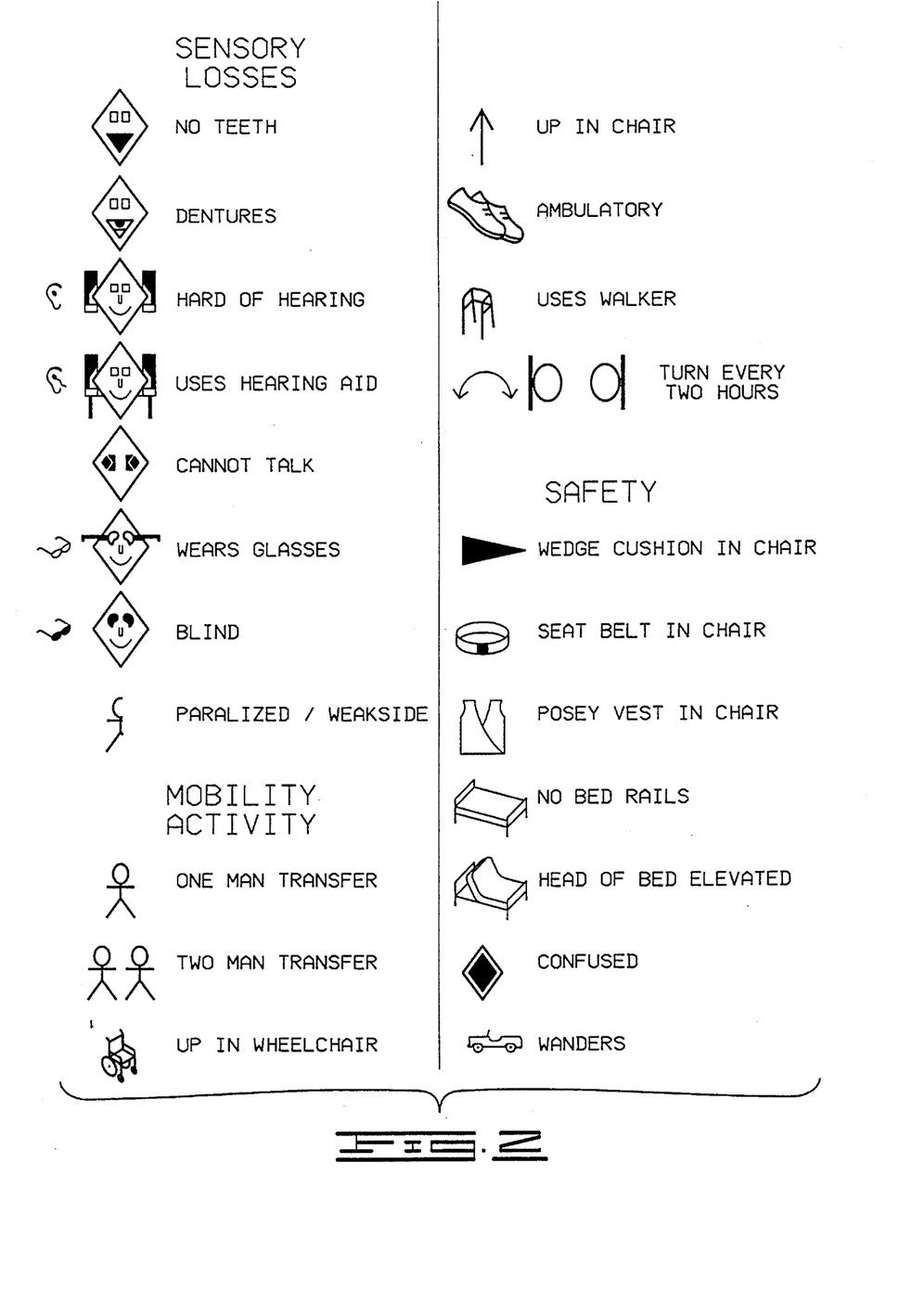
FIGS. 2 and 2A are diagrammatic views illustrating some of the preferred patient care pictorial symbols utilized in the patient care information assembly of FIG. 1, along with a word description of each such symbol.
Figure 2A:
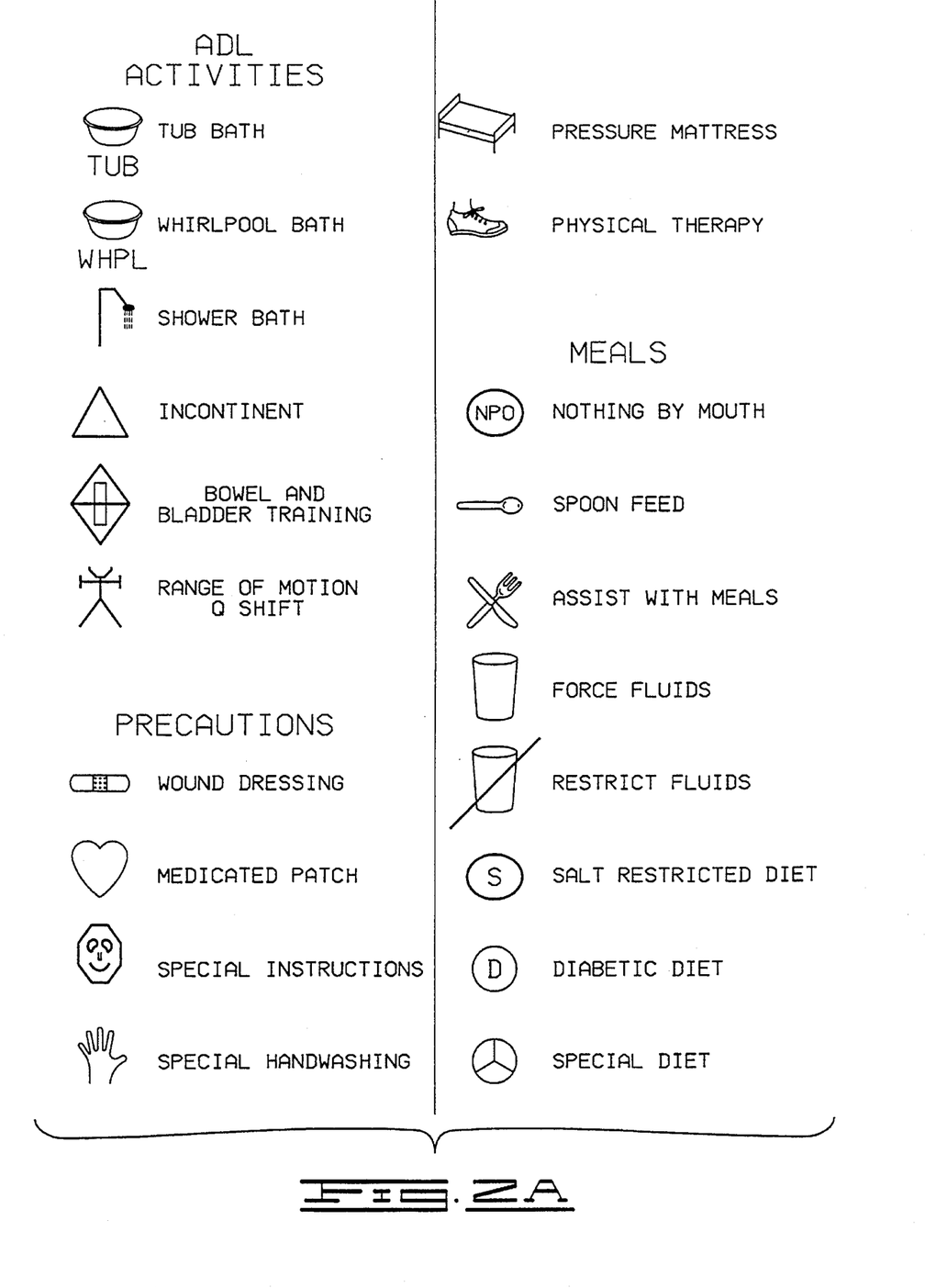

Preferred patient care pictorial symbols 14 are shown in FIGS. 2 and 2A along with the patient care information associated with each of the symbols 14.

As shown in FIGS. 2 and 2A, the patient care pictorial symbols 14 in one embodiment are divided into categories: "SENSORY LOSSES", "PRECAUTIONS", "SAFETY", "ADL ACTIVITIES", "MOBILITY ACTIVITY", and "MEALS". The particular symbols 14 shown in FIGS. 2 and 2A illustrate the concept of the present invention and, in a particular application, one may use different pictorial symbols. It is significant to note that the patient care pictorial symbols 14 shown in FIGS. 2 and 2A are pictorial in nature and preferably do not include printed words explaining such symbols on the patient care blocks 16. The reason for this significance is a matter of courtesy and sensitivity to the patient's condition and feelings.

Most of the patient care pictorial symbols 14 shown in FIGS. 2 and 2A are self explanatory to professional care providers particularly when considered with the written explanations associated with each of the patient care pictorial symbols 14 shown in FIGS. 2 and 2A.

For example, the patient care pictorial symbol 14 shown in FIG. 2 under the heading SENSORY LOSSES indicating NO TEETH indicates to the care provider this selected patient does not have teeth and there is no need for the care provider to search for missing dentures, for example. In addition, this symbol 14 indicates to the care provider that foods which can not be eaten without teeth should not be provided to this particular selected patient.

The patient care pictorial symbol 14 shown in FIG. 2 under SENSORY LOSSES indicating DENTURES indicates to the care provider that the care provider should find the dentures and provide them to this particular selected patient and that the dentures periodically should be taken out and cleaned.

The patient care pictorial symbol 14 shown in FIG. 2 under the heading SENSORY LOSSES indicating PARALYZED/WEAK SIDE indicates to the care provider that caution should be taken when attempting to stand this particular selected patient in an upright position.

The patient care pictorial symbol 14 shown in FIG. 2A under the heading PRECAUTIONS indicating WOUND DRESSING indicates that the care provider should check with personnel to determine whether or not such dressing should be removed when bathing this particular selected patient, for example.

The patient care pictorial symbol 14 shown in FIG. 2A under the heading PRECAUTIONS indicating MEDICATED PATCH indicates to the care provider that this particular patch should not be removed.

The patient care pictorial symbol 14 shown in FIG. 2A under the heading PRECAUTIONS indicating SPECIAL HAND WASHING indicates to the care provider that the care provider should wash their hands before and after having contact with this particular selected patient either because this patient has low immunity, for example, or to prevent transmission of disease from the patient to the care provider or from the care provider to the patient.

The patient care pictorial symbol 14 shown in FIG. 2A under the heading PRECAUTIONS indicating PRESSURE MATTRESS indicates that this particular selected patient has a pressure relieving type of mattress and, if wet for example, the care provider needs to replace it or see that it is operating or make sure that in fact such a pressure mattress is on this patient's bed.

The patient care pictorial symbol 14 shown in FIG. 2A under the heading PRECAUTIONS indicating PHYSICAL THERAPY indicates to the care provider that the care provider should get this particular selected patient ready to go to physical therapy and indicates to the care provider that in fact this particular selected patient is involved in physical therapy.

The patient care pictorial symbol 14 shown in FIG. 2 under the heading SAFETY indicating WEDGE CUSHION IN CHAIR indicates to the care provider that there is some positioning device in the wheelchair of this particular selected patient and the care provider should make sure that such positioning device is in fact in place.

The patient care pictorial symbol 14 shown in FIG. 2 under the heading SAFETY indicating POSEY VEST IN CHAIR indicates to the care provider that a posey type restraint is in this particular selected patient's wheelchair and that this patient should be restrained via such device.

The patient care pictorial symbol 14 shown in FIG. 2A under the heading ADL ACTIVITIES indicating RANGE OF MOTION Q SHIFT indicates to the care provider that there is a need to exercise the extremities of this particular selected patient at periodic time intervals.

The patient care pictorial symbol 14 shown in FIG. 2 under the heading MOBILITY ACTIVITY indicating UP IN WHEELCHAIR indicates to the care provider that this particular selected patient is wheelchair fast.

The patient care pictorial symbol 14 shown in FIG. 2 under the heading MOBILITY ACTIVITY indicating UP IN CHAIR indicates to the care provider that this particular selected patient needs to be placed in a chair when taken out of bed.

The patient care pictorial symbol 14 shown in FIG. 2 under the heading MOBILITY ACTIVITY indicating TURN EVERY TWO HOURS indicates to the care provider that this particular selected patient needs to be repositioned in the bed or in a chair every two hours.

The patient care pictorial symbol 14 shown in FIG. 2A under the heading MEALS indicating FORCE FLUIDS indicates to the care provider that this particular selected patient should be encouraged to drink fluids.

The patient care pictorial symbol 14 shown in FIG. 2A under the heading MEALS indicating RESTRICT FLUIDS indicates to the care provider that this particular selected patient is to be given only a limited amount of fluids and that the care provider should not leave a water pitcher at the bedside of this selected patient, for example.

The patient care pictorial symbol 14 shown in FIG. 2A under the heading MEALS indicating DIABETIC DIET indicates to the care provider that significant other care is required with respect to this particular selected patient relating to a diabetic diet and other matters associated with a diabetic condition.

Care providers in hospitals and nursing homes or other care environments are dedicated, professional individuals who desire and who are strongly motivated to provide quality care to their patients. However, due to lack of time or proper instruction or any one of a number of other reasons, the care provider for a particular patient may not always be informed of special care needs associated with that patient. When not properly informed, the care provider cannot provide quality care and unintentionally can do things which are detrimental to the patient. The patient care information system 10 of the present invention is intended to provide immediate information to the care provider relating to a particular selected patient's individual care needs.

In operation, the facility initially selects predetermined ones of the patient care blocks 16 having patient care pictorial symbols 14 thereon related to the care of a selected patient. These particular patient care blocks 16 are designated for descriptive purposes as selected patient care blocks 16.

The facility may utilize a photograph of the particular patient (selected patient). This photograph or picture 52 then is inserted in a direction 54 (FIG. 1) into the picture receiving channel 50. The picture 52 of the selected patient is secured to the upper surface 24 of the picture frame 22 by way of the tabs, 40, 42, 44, 46, and 48. The tab 48 is located or positioned to limit the movement of the picture 52 in the picture receiving channel 50 in the direction 54 and cooperates to hold the picture 52 on the upper surface 24 of the patient frame 22 when the patient frame 22 is held in an upright position.

Figure 3:
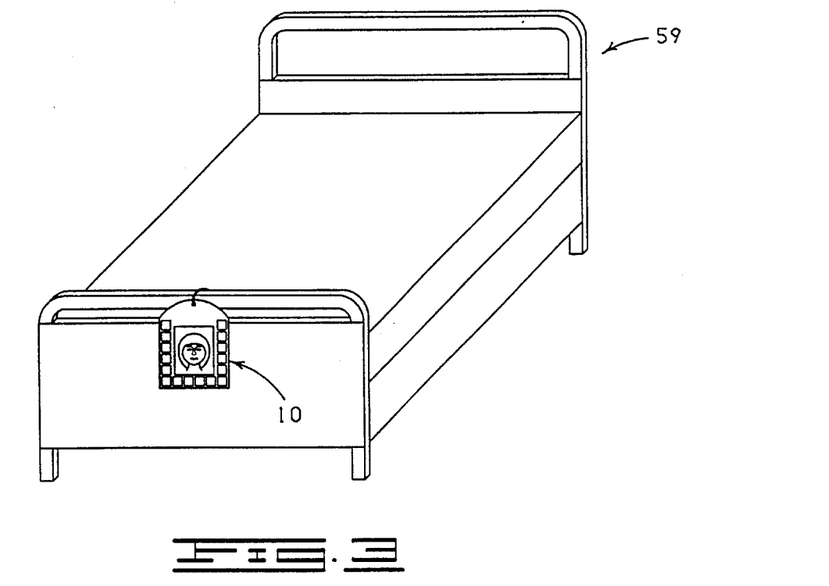
FIG. 3 is a diagrammatic view showing the patient care information assembly of FIG. 1 in an assembled condition attached to a patient's bed.

The selected patient care blocks 16 then are magnetically and removably affixed or attached to the upper surface 24 of the patient frame 22, as shown in FIG. 3. The patient frame 22 is sized and the tabs 40, 42, 44, 46, and 48 are positioned on the upper surface 24 of the patient frame 22 to provide three patient care block receiving spaces 54, 56, and 58, as shown in FIGS. 1 and 3. In one preferred embodiment, as shown in the drawings, the patient care block receiving spaces 54 and 56 each are sized so that six patient care blocks 16 may be disposed along each side of the patient frame 22 and four additional patient care blocks 16 may be disposed along a lower edge of the patient frame 22 generally between the patient care blocks 16 disposed on each side of the patient frame 22. In any event, the patient's picture 52 and the selected patient care blocks 16 having patient care pictorial symbols 14 thereon associated with the selected patient are attached to the patient frame 22.

The patient frame 22 with the selected patient care blocks 16 removably connected thereto and the patient picture 52 removably connected thereto then is positioned in the vicinity of the selected patient so that the patient care pictorial symbols 14 associated with the selected patient care blocks 16 are visible or readily available to the care provider providing care to that particular selected patient.

For example and as shown in FIG. 3, the patient frame 22 with the selected patient care blocks 16 and the patient's picture 52 disposed thereon may be attached to a rail on a patient's bed 59 by way of the strap 34. The patient frame 22 is secured to the rail of the bed 59 by way of the hook and loop fastening elements 36 and 38 associated with the strap 34. In this manner, the patient care pictorial symbols 14 associated with the selected patient care blocks 16 are readily visible to the care provider rendering care to that particular selected patient.

Figure 4:
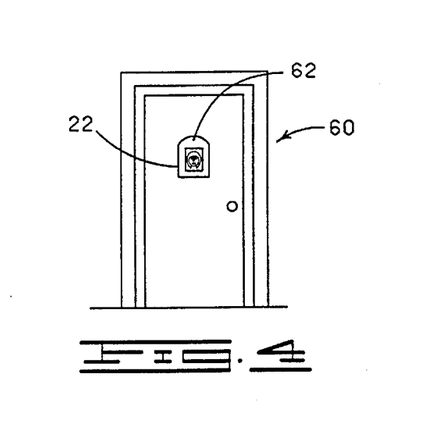
FIG. 4 is a diagrammatic view showing an assembled patient care information assembly attached to a door of a patient's room.

In one other embodiment, the patient frame 22 with the patient's picture 52 and the selected patient care blocks 16 disposed thereon may be affixed to the inside or the outside of a door 60 (FIG. 4) associated with the selected patient's room by a nail type element 62 secured to the door and extending through the opening 32 in the tab 30 portion of the patient frame 22.

Figure 5:
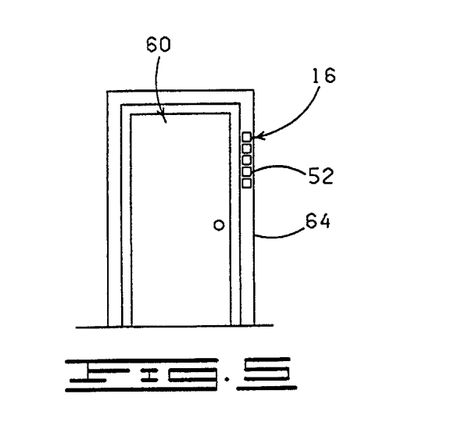
FIG. 5 is a diagrammatic view showing a patient's door with modified patient care block assemblies affixed to the frame of a patient's door.

In many instances, the patient's door 60 includes a metal frame 64 associated therewith, shown in FIG. 5. In those instances, the selected patient care blocks 16 may be magnetically and removably connected to the door frame 64 (FIG. 5). In this last mentioned embodiment, the patient's picture 52 also may be affixed to a block constructive of a magnet material and affixed to the door frame 64 shown in FIG. 5.

Figure 6:
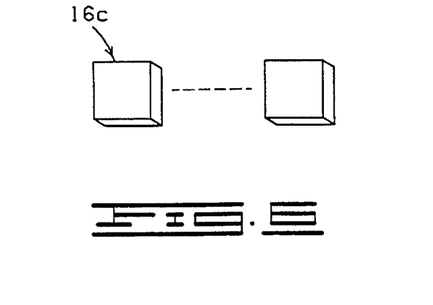
FIG. 6 is a perspective view showing modified patient care blocks.
Figure 7:
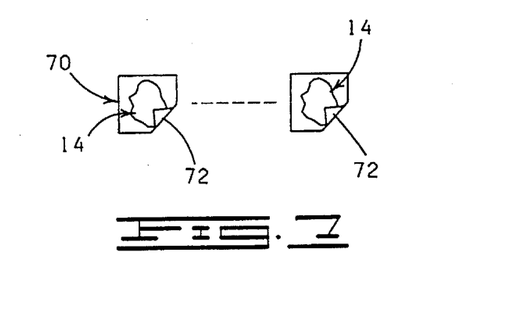
FIG. 7 is a view showing patient cards which either are attached to the patient care blocks shown in FIG. 6 or attached to the patient frame shown in FIGS. 1, 3 and 4 or attached and displayed near or in the vicinity of the selected patient such as by placing the patient cards on the door frame, as shown in FIG. 5.

In lieu of printing the patient care pictorial symbols 14 on the patient care blocks 16, the patient care information assembly 10 may include a plurality of patient care blocks 16c (FIG. 6) which are simply blocks constructed of a magnet material. In this embodiment, the patient care information assembly 10 includes a plurality of patient cards 70 (FIG. 7). Each of the patient cards 70 has one of the patient care pictorial symbols 14 printed on an upper surface thereof and an adhesive or other bonding agent 72 disposed on a lower surface thereof. In this embodiment, the patient cards 70 are bondingly connected to the upper surface of the patient care blocks 16c. In the alternative, the patient cards 70 having the bonding material 72 thereon may be bondingly connected directly to the patient frame 22 or to any other surface in the vicinity of the patient such as the door frame 64 (FIG. 5) for example. In this last mentioned embodiment the patient cards 70 would comprise the patient care block assemblies 12.

The patient care block assemblies (FIG. 1 or FIGS. 6 and 7 or FIG. 7 alone) may also be placed or displayed on the door of a bathroom associated with the selected patient's room.

In a preferred embodiment, the patient care block assemblies 12 are square or rectangularly shaped and each has a width 80 (FIG. 1) and a length 82 (FIG. 1). The length 80 and the width 82 each are in a range from about ½ inch to about 4 inches. The size of the patient care block assemblies 12 as just described is significant in that such patient care block assemblies 12 are large enough to convey the required care information to the care provider and yet small enough so as not to call undue attention to a particular patient's special care needs.

In a total hospital or nursing environment, it is contemplated that the hospital or nursing care facility would have a plurality of the patient frames 22 and the plurality of the patient care block assemblies 12 comprising the patient care blocks 16 or 16c or the patient cards 70. The facility then may provide a picture 52 of each of the selected patients within the facility. The facility then would select patient care pictorial symbols 14 which apply to each of the selected patients. The patient's picture along with the patient care pictorial symbols 14 associated with each of the selected patients then would be displayed in the vicinity of the selected patient in any of the manners described herein.

Changes may be made in the construction and the operation of the various components, elements and assemblies described herein and changes may be made in the steps or the sequence of steps of the methods described herein without departing from the spirit and scope of the invention as defined in the following claims.

What is claimed is:

1. A method for improving the delivery of individualized nursing care for patients, the method comprising:

(a) providing a plurality of patient care block assemblies, each patient care block assembly having a different patient care pictorial symbol thereon indicating a single patient care information relating to the providing of individualized nursing care for a patient;

(b) selecting a plurality of the patient care block assemblies having different patient care pictorial symbols thereon related to the individualized nursing care of a selected patient and designating the ones of the patient care block assemblies so selected as selected patient care block assemblies;

(c) displaying the selected patient care block assemblies in the vicinity of the selected patient where the patient care pictorial symbols on the selected patient care block assemblies are visible to a care provider;

(d) viewing by the care provider, the selected patient care block assemblies so that the patient care pictorial symbols alone provide immediate information to the care provider; and (e) rendering individualized nursing care to the selected patient in accordance with the selected patient care block assemblies.

2. The method of claim 1 further comprising the step of:
repeating steps (b) and (c) for each of a plurality of selected patients.

3. The method of claim 1 wherein the step of providing the patient care block assemblies is defined further as providing the patient care block assemblies with each patient care block assembly having a length in a range from about one half inch to about four inches and a width in a range from about one half inch to about four inches.

4. A method for improving the delivery of individualized nursing care for patients, the method comprising:

(a) providing a patient frame;

(b) providing a plurality of patient care block assemblies, each patient care block assembly having a different patient care pictorial symbol thereon indicating a single patient care information relating to the providing of individualized nursing care for a patient;

(c) selecting a plurality of the patient care block assemblies having different patient care pictorial symbols thereon related to the individualized nursing care of a selected patient and designating the ones of the patient care block assemblies so selected as selected patient care block assemblies;

(d) placing the selected patient care block assemblies on the patient frame;

(e) placing the patient frame with the selected patient care block assemblies thereon in the vicinity of the selected patient where the patient care pictorial symbols on the selected patient care block assemblies are displayed and visible to a care provider;

(f) viewing, by the care provider, the selected patient care block assemblies so that the patient care pictorial symbols alone provide immediate information to the care provider; and (g) rendering individualized nursing care to the selected patient in accordance with the selected patient care block assemblies.

5. The method of claim 4 further comprising:

repeating steps (c), (d) and (e) for each of a plurality of selected patients.

6. The method of claim 4 wherein the step of providing the patient care block assemblies is defined further as providing the patient care block assemblies with each patient care block assembly having a length in a range from about one half inch to about four inches and a width in a range from about one half inch to about four inches.

7. A method for improving the delivery of individualized nursing care for patients, the method comprising:

(a) providing a patient frame;

(b) providing a plurality of patient care block assemblies, each patient care block assembly having a different patient care pictorial symbol thereon indicating a single patient care information relating to the providing of individualized nursing care for a patient;

(c) selecting a plurality of the patient care block assemblies having different patient care pictorial symbols thereon related to the individualized nursing care of a selected patient and designating the ones of the patient care block assemblies so selected as selected patient care block assemblies;

(d) providing a picture of the selected patient;

(e) supporting the picture of the selected patient on the frame;

(f) disposing the selected patient care block assemblies on the patient frame;

(g) positioning the patient frame with the selected patient care block assemblies and the patient picture thereon in the vicinity of the selected patient whereby the patient care pictorial symbols on the selected patient care block assemblies are visible to a care provider;

(h) viewing, by the care provider, the selected patient care block assemblies so that the patient care pictorial symbols alone provide immediate information to the care provider; and (i) rendering individualized nursing care to the selected patient in accordance with the selected patient care block assemblies.

8. The method of claim 7 further comprising: repeating steps (c), (d), (e), (f) and (g) for each of a plurality of selected patients.

9. The method of claim 7 wherein the step of providing the patient care block assemblies is defined further as providing the patient care block assemblies with each patient care block assembly having a length in a range from about one half inch to about four inches and a width in a range from about one half inch to about four inches.

10. A method for improving the delivery of individualized nursing care for patients, the method comprising:

(a) providing a plurality of patient care block assemblies with each patient care block assembly being at least partially constructed of a magnetic material and having a different patient care pictorial symbol thereon indicating a single patient care information relating to the providing of individualized nursing care for a patient;

(b) selecting a plurality of the patient care block assemblies having patient care pictorial symbols thereon related to the individualized nursing care of a selected patient and designating the ones of the patient care block assemblies so selected as selected patient care block assemblies; and (c) magnetically connecting the selected patient care block assemblies to a structure in the vicinity of the selected patient where the patient care pictorial symbols on the selected patient care block assemblies are visible to a care provider;

(d) viewing, by the care provider, the selected patient care block assemblies so that the patient care pictorial symbols alone provide immediate information to the care provider; and (e) rendering individualized nursing care to the selected patient in accordance with the selected patient care block assemblies.

11. The method of claim 10 further comprising the step of:

repeating steps (b) and (c) for each of a plurality of selected patients.

12. The method of claim 10 wherein the step of providing the patient care block assemblies is defined further as providing the patient care block assemblies with each patient care block assembly having a length in a range from about one half inch to about four inches and a width in a range from about one half inch to about four inches.

13. A method for improving the delivery of individualized nursing care for patients, the method comprising:

(a) providing a patient frame being constructed of a metal;

(b) providing a plurality of patient care block assemblies with each patient care block assembly being at least partially constructed of a magnetic material and having a different patient care pictorial symbol thereon indicating a single patient care information relating to the providing of individualized nursing care for a patient;

(c) selecting a plurality of the patient care block assemblies having different patient care pictorial symbols thereon related to the individualized nursing care of a selected patient and designating the ones of the patient care block assemblies so selected as selected patient care block assemblies;

(d) magnetically connecting the selected patient care block assemblies to the patient frame; and (e) placing the patient frame with the selected patient care block assemblies thereon in the vicinity of the selected patient where the patient care pictorial symbols on the selected patient care block assemblies are displayed and visible to a care provider;

(f) viewing, by the care provider, the selected patient care block assemblies so that the patient care pictorial symbols alone provide immediate information to the care provider; and (g) rendering individualized nursing care to the selected patient in accordance with the selected patient care block assemblies.

14. The method of claim 13 further comprising:
repeating steps (c), (d) and (e) for each of a plurality of selected patients.

15. The method of claim 13 wherein the step of providing the patient care block assemblies is defined further as providing the patient care block assemblies with each patient care block assembly having a length in a range from about one half inch to about four inches and a width in a range from about one half inch to about four inches.

16. A method for improving the delivery of individualized nursing care for patients, the method comprising:
   (a) providing a patient frame being constructed of a metal;
   (b) providing a plurality of patient care block assemblies with each patient care block assembly being at least partially constructed of a magnetic material, each patient care block assembly having a different patient care pictorial symbol thereon indicating a single patient care information relating to the providing of individualized nursing care for a patient;
   (c) selecting a plurality of the patient care block assemblies having different patient care pictorial symbols thereon related to the individualized nursing care of a selected patient and designating the ones of the patient care block assemblies so selected as selected patient care block assemblies;
   (d) providing a picture of the selected patient;
   (e) supporting the picture of the selected patient on the frame;
   (f) magnetically connecting the selected patient care block assemblies to the patient frame;
   (g) placing the patient frame with the selected patient care block assemblies and the patient picture thereon in the vicinity of the selected patient where the patient care pictorial symbols on the selected patient care block assemblies are visible to a care provider;
   (h) viewing by the care provider, the selected patient care block assemblies so that the patient care pictorial symbols alone provide immediate information to the care provider; and
   (i) rendering individualized nursing care to the selected patient in accordance with the selected patient care block assemblies.

17. The method of claim 16 further comprising:
repeating the steps (c), (d), (e), (f), and (g) for each of a plurality of selected patients.

18. The method of claim 16 wherein the step of providing the patient care block assemblies is defined further as providing the patient care block assemblies with each patient care block assembly having a length in a range from about one half inch to about four inches and a width in a range from about one half inch to about four inches.

19. A method for improving the delivery of individualized nursing care for patients, the method comprising:
   (a) providing a patient frame;
   (b) providing a plurality of patient care blocks;
   (c) providing a plurality of patient cards, each patient card having a different patient care pictorial symbol thereon indicating a single patient care information relating to the providing of individualized nursing care for a patient;
   (d) selecting a plurality of the patient cards having different patient care pictorial symbols thereon related to the individualized nursing care of a selected patient;
   (e) placing each of the patient cards related to the care of the selected patient on one of the patient care blocks to provide selected patient care block assemblies;
   (f) placing the selected patient care block assemblies on the patient frame;
   (g) placing the patient frame with the selected patient care block assemblies thereon in the vicinity of the selected patient where the patient care pictorial symbols on the selected patient care block assemblies are displayed and visible to a care provider;
   (h) viewing, by the care provider, the selected patient care block assemblies so that the patient care pictorial symbols alone provide immediate information to the care provider; and
   (i) rendering individualized nursing care to the selected patient in accordance with the selected patient care block assemblies.

20. The method of claim 19 further comprising:
repeating steps (d), (e), (f) and (g) for each of a plurality of selected patients.

21. The method of claim 19 wherein the step of providing the patient care blocks is defined further as providing the patient care blocks with each patient care block having a width in a range from about one half inch to about four inches and a length in a range from about one half inch to about four inches.

22. A method for improving the delivery of individualized nursing care for patients, the method comprising:
   (a) providing a patient frame;
   (b) providing a plurality of patient care blocks;
   (c) providing a plurality of patient cards, each patient card having a different patient care pictorial symbol thereon indicating a single patient care information relating to the providing of individualized nursing care for a patient;
   (d) selecting a plurality of the patient cards having different patient care pictorial symbols thereon related to the individualized nursing care of a selected patient and placing each of the selected patient cards on one of the patient care blocks to provide selected patient care block assemblies;
   (e) providing a picture of the selected patient;
   (f) supporting the picture of the selected patient on the frame;
   (g) disposing the selected patient care block assemblies on the patient frame;
   (h) positioning the patient frame with the selected patient care block assemblies and the patient picture thereon in the vicinity of the selected patient whereby the selected patient care pictorial symbols are visible to a care provider;
   (i) viewing, by the care provider, the selected patient care block assemblies so that the patient care pictorial symbols alone provide immediate information to the care provider; and
   (j) rendering individualized nursing care to the selected patient in accordance with the selected patient care block assemblies.

23. The method of claim 22 further comprising:
repeating steps (d), (e), (f), (g) and (h) for each of a plurality of selected patients.

24. The method of claim 22 wherein the step of providing the patient care blocks is further defined further as providing the patient care blocks with each patient care block having a width in a range from about one half inch to about four inches and a length in a range from about one half inch to about four inches.

25. A method for improving the delivery of individualized nursing care for patients, the method comprising:

(a) providing a plurality of patient care blocks;

(b) providing a plurality of patient cards with each patient card having a different patient care pictorial symbol thereon indicating a single patient care information relating to the providing of individualized nursing care for a patient;

(c) selecting a plurality of the patient cards having different patient care pictorial symbols thereon related to the individualized nursing care of a selected patient and placing each of the selected patient cards on one of the patient care blocks to provide selected patient care block assemblies;

(d) displaying the selected patient care block assemblies in the vicinity of the selected patient whereby the patient care pictorial symbols on the selected patient care block assemblies are visible to a care provider;

(e) viewing, by the care provider, the selected patient care block assemblies so that the patient care pictorial symbols alone provide immediate information to the care provider; and (f) rendering individualized nursing care to the selected patient in accordance with the selected patient care block assemblies.

26. The method of claim 25 further comprising:

repeating steps (c) and (d) for each of a plurality of selected patients.

27. The method of claim 25 wherein the step of providing the patient care blocks is further defined as providing the patient care blocks with each of the patient care blocks having a width in a range from about one half inch to about four inches and a length in a range from about one half inch to about four inches.

* * * * *